(12) United States Patent
Hirai et al.

(10) Patent No.: US 6,844,427 B2
(45) Date of Patent: Jan. 18, 2005

(54) METHOD FOR REMOVING THE TRANSFORMING GROWTH FACTOR-β BY ADSORPTION

(75) Inventors: Fumiyasu Hirai, Ibaraki (JP); Tamiji Fujimoto, Settsu (JP); Shigeo Furuyoshi, Kobe (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/773,598

(22) Filed: Feb. 2, 2001

(65) Prior Publication Data

US 2001/0021525 A1 Sep. 13, 2001

(30) Foreign Application Priority Data

Feb. 14, 2000 (JP) ........................................ 2000-035168

(51) Int. Cl.$^7$ ........................ A23J 1/00; C07K 14/00; A61K 39/00
(52) U.S. Cl. ...................... 530/422; 530/412; 530/350; 424/198.1
(58) Field of Search ............................... 530/412, 422, 530/350; 424/198.1

(56) References Cited

U.S. PATENT DOCUMENTS

| | | | |
|---|---|---|---|
| 4,721,730 A | | 1/1988 | Furuyoshi et al. ............ 521/53 |
| 4,774,322 A | * | 9/1988 | Seyedin et al. ............... 514/21 |
| 4,931,548 A | * | 6/1990 | Lucas et al. ................. 514/885 |
| 5,231,178 A | * | 7/1993 | Holtz et al. ................. 530/399 |
| 5,322,933 A | * | 6/1994 | Davies et al. ............... 530/324 |
| 6,270,994 B1 | * | 8/2001 | Miyazono et al. ........ 435/252.1 |

FOREIGN PATENT DOCUMENTS

| | | |
|---|---|---|
| EP | 0 323 842 | 1/1989 |
| EP | 0 722 773 | 1/1996 |
| EP | 0 723 794 | 1/1996 |
| EP | 0 819 439 | 1/1997 |
| EP | 0 993 834 | 4/1998 |
| JP | 7-31875 | 2/1995 |

OTHER PUBLICATIONS

Leo A., et al: "Partition Coefficients and Their Uses" *Chemical Reviews,* US, American Chemical Society, Washington, D.C., vol. 71, No. 6, Dec. 1, 1971.

* cited by examiner

*Primary Examiner*—Janet Andres
(74) *Attorney, Agent, or Firm*—Westerman, Hattori, Daniels & Adrian LLP

(57) ABSTRACT

An adsorbent suitable for adsorption of a transforming growth factor-β (TGF-β) comprising a compound which has a log P value of at least 2.50 wherein P is a partition coefficient in an octanol-water system and which is immobilized on a water-insoluble carrier. TGF-β present in a body fluid can be efficiently removed by bringing the body fluid into contact with the adsorbent.

2 Claims, 2 Drawing Sheets

METHOD FOR REMOVING THE TRANSFORMING GROWTH FACTOR-β BY ADSORPTION

BACKGROUND OF THE INVENTION

The present invention relates to an adsorbent for removing transforming growth factor-β (hereinafter referred to as "TGF-β") from body fluids by adsorption, a method for removing TGF-β by using the adsorbent, and an adsorber for TGF-β comprising the adsorbent packed.

TGF-β was purified at the beginning as a growth factor which had a transforming activity for fibroblast, and after that, TGF-β was found to be a substance which had potent inhibitory effects on growth of many kinds of cells. It is also known that TGF-β is deeply involved in cell differentiation, cell migration and cell adhesion as well as control of cell growth, and further, it plays an extremely important part in ontogeny, tissue remodeling, healing of injury, inflammation, immunity and others. TGF-β is a dimeric protein having a molecular weight of about 25,000. Three kinds of TGF-β, i.e., TGF-β1, TGF-β2 and TGF-β3, are known in mammal. They have a 70–80% homology to each other and form a TGF-β family. Abnormal production of TGF-β has been reported on many kinds of diseases. Concerning hemopathy, for example, production of TGF-β increases in acute megakaryocytic leukemia, adult T cell leukemia or Hodgkin's disease, and the relation between the increased production and conditions of each disease has been discussed.

Recently, it is reported that TGF-β is one of substances causing chronic fatigue syndrome which is pathologic fatigue.

Chronic fatigue syndrome (hereinafter referred to as "CFS") causes intense systemic malaise of unknown origin, febricula, headache, a feeling of exhaustion, a neuropsychic symptom such as thinking disorder or depression, and so on to a person who has lived a healthy life. Because these symptoms continue over a long term, the patient cannot live a healthy life as a member of society. Kuratsune et al. report that the concentration of TGF-β in serum rises in the majority of CFS patients. Therefore, it has been considered that TGF-β occupies an important part in the critical cascade of chronic fatigue syndrome. A treatment of CFS by controlling TGF-β in blood is expected, but there has not been known any way of absorbing and removing TGF-β from body fluids. Therefore, a way of absorbing and removing TGF-β has been much desired. Further, its application to general fatigue is considered as well as pathologic CFS and, therefore, a way of absorbing and removing TGF-β is desired over wider fields.

An object of the present invention is to provide an adsorbent capable of efficiently removing TGF-β present in body fluids.

A further object of the present invention is to provide a method for removing TGF-β from body fluids by adsorption with the adsorbent.

A still further object of the present invention is to provide a device for removing TGF-β from body fluids by adsorption with the adsorbent.

These and other objects of the present invention will become apparent from the description hereinafter.

SUMMARY OF THE INVENTION

The present inventors made an intensive study on adsorbents capable of efficiently removing TGF-β present in body fluids, and have now found that an adsorbent comprising a water-insoluble carrier and a compound having a log P value of at least 2.50 immobilized on the carrier can efficiently adsorb and remove TGF-β present in body fluids.

Thus, in accordance with the present invention, there is provided an adsorbent for TGF-β comprising a water-insoluble carrier and a compound having a log P value of at least 2.50 wherein P is a partition coefficient in an octanol-water system, the compound being immobilized on the carrier.

In a preferable embodiment of the present invention, the water-insoluble carrier is a water-insoluble porous carrier. A water-insoluble porous carrier having an exclusion limit of from 5,000 to 600,000 is more preferred.

The present invention also provides a method for removing TGF-β in body fluid, which comprises bringing a body fluid into contact with an adsorbent for TGF-β comprising a water-insoluble carrier and a compound having a log P value of at least 2.50 wherein P is a partition coefficient in an octanol-water system, the compound being immobilized on the carrier.

Further, the present invention provides an adsorber for removing TGF-β comprising a container having an inlet and an outlet for a body fluid and a means for preventing an adsorbent from flowing out of the container, and an adsorbent for TGF-β packed in the container, the adsorbent comprising a water-insoluble carrier and a compound immobilized on the carrier and having a log P value of at least 2.50 wherein P is a partition coefficient in an octanol-water system.

DETAILED DESCRIPTION

Figure 1:
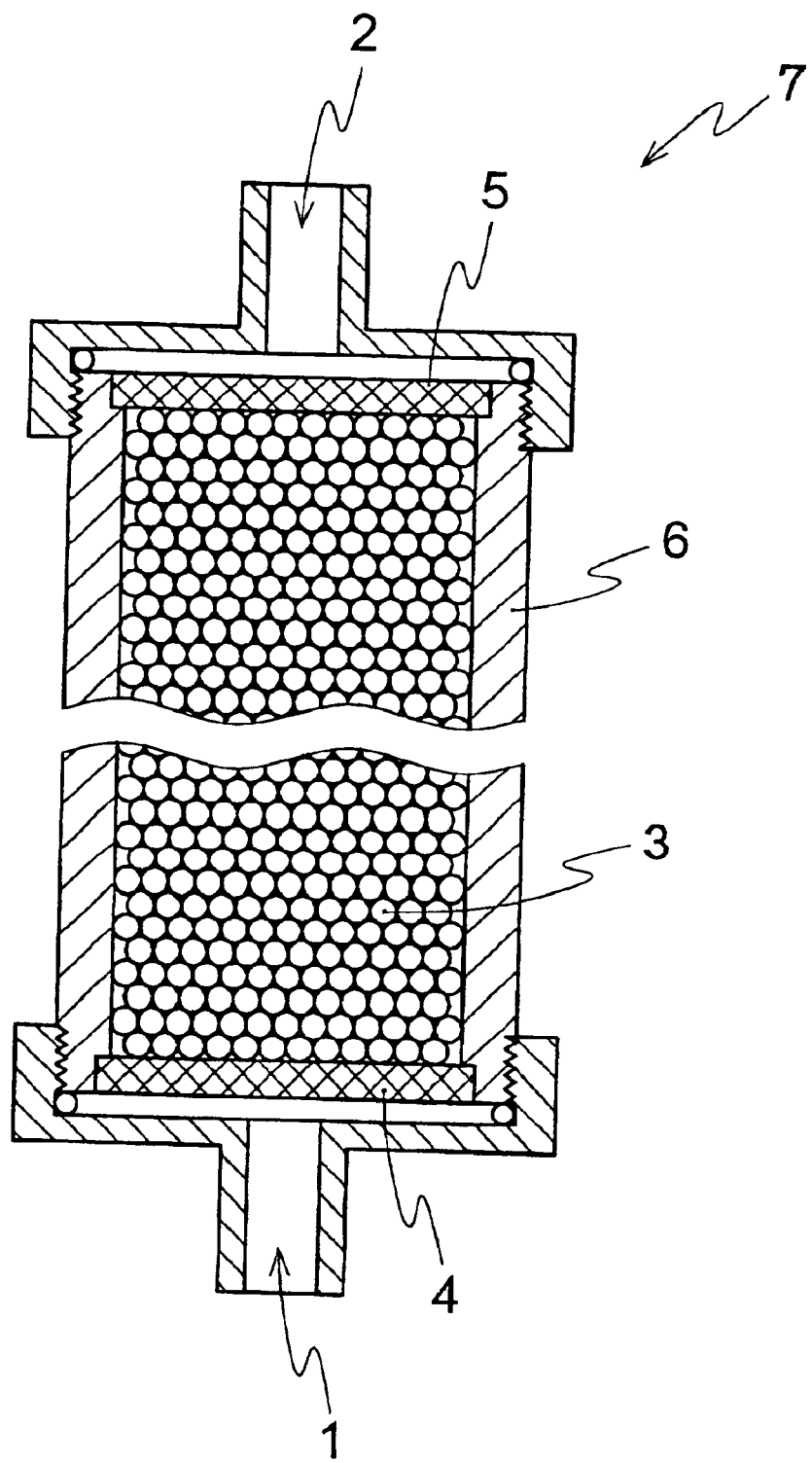
FIG. 1 is a schematic cross section view showing an example of an adsorber suitable for removing TGF-β according to the present invention.

The "TGF-β" as referred to in the present invention is a protein having a molecular weight of about 25,000 and comprising 112 amino acids.

Also, the term "body fluid" as used herein means blood, plasma, serum, ascites, lymph, synovia and fractions obtained from them, and other liquid components derived from a living body.

The adsorbent of the present invention comprises a compound having a log P value of at least 2.50 that is immobilized on a water-insoluble carrier. The log P value is a parameter which indicates the hydrophobicity of a compound. A typical partition coefficient P in an octanol-water system is determined as follows: At first, a compound is dissolved in octanol (or water) and an equal amount of water (or octanol) is added thereto. After shaking the mixture for 30 minutes with a Griffin flask shaker (made by Griffin & George Ltd.), the mixture is centrifuged for 1 to 2 hours at 2,000 r.p.m. The respective concentrations of the compound in both octanol and water layers are measured at room temperature and atmospheric pressure by various methods such as spectroscopic method or GLC, and the partition coefficient P is obtained from the following equation.

$$P = C_{oct}/C_w$$

Coct: concentration of the compound in the octanol layer

Cw: concentration of the compound in the water layer

In the present invention are used compounds, the logarithmic value of the partition coefficient P as obtained in the above manner (log P value) of which is 2.50 or more.

Until now, many investigators have determined log P values of various compounds and the found values of the log P are put in order by C. Hansch et al ("PARTITION COEFFICIENTS AND THEIR USES"; Chemical Reviews, 71, page 525 (1971)). These values can be used herein.

As to compounds whose found values are unknown, calculated values (Σf) obtained by using hydrophobic fragmental constants f shown in R. F. Rekker's book ("THE HYDROPHOBIC FRAGMENTAL CONSTANT", Elsevier Sci. Pub. Corn., Amsterdam, 1977) can be a good guide. The hydrophobic fragmental constants f are values showing the hydrophobicity of various fragments determined by a statistical treatment of many found values of log P. It is reported that the sum of f values of respective fragments which constitute a compound approximately agree with the log P value of the compound. Accordingly, in case that the log P value of a compound is not known, it can be determined by the Σf value calculated from the f values of fragments of the compound.

In investigating compounds effective for adsorbing TGF-β, compounds having various log P values were immobilized on a water-insoluble carrier and the adsorption ability thereof were examined with respect to TGF-β. As a result, it has been found that compounds having a log P value of 2.50 or more, preferably 2.80 or more, more preferably 3.00 or more, are effective for adsorption of TGF-β, and that compounds having a log P value of less than 2.5 hardly show an adsorption ability for TGF-β. For example, in the case of immobilizing an alkylamine on a water-insoluble carrier, it has been found that the adsorption ability for TGF-β is enhanced to a great extent if the alkylamine to be immobilized is changed from n-hexyllamine (log P=2.06)) to n-octylamine (log P=2.90). From these results, it is assumed that the adsorption ability of the adsorbent according to the present invention with respect to TGF-β is based on a hydrophobic interaction between TGF-β and an atomic group introduced onto a carrier by immobilization of a compound having a log p value of 2.50 or more.

In the present invention, compounds to be immobilized onto a water-insoluble carrier can be employed without particular limitation so long as they have a log P value of 2.50 or more. However, in case of immobilizing a compound onto a carrier by a chemical bonding method, a part of the compound is often eliminated. When the eliminated group greatly contributes to the hydrophobicity of the compound, that is to say, when the hydrophobicity of an atomic group immobilized onto the carrier becomes smaller than Σf=2.50 due to the elimination, such a compound is not suitable as the compound to be used in the present invention from the viewpoint of the gist of the present invention. A typical example thereof is a case where isopentyl benzoate (Σf= 4.15) is immobilized onto a carrier having hydroxyl group by transesterification. In this case, the atomic group which is actually immobilized onto the carrier is $C_6H_5$—CO—, the Σf value of which is 1 or less. Whether such compounds are suitable or not as a compound used in the present invention may be judged by determining whether the log P value of a compound obtainable by substituting the eliminating part by hydrogen is not less than 2.50 or not.

Among compounds having a log P value of 2.50 or more, preferable are compounds having a functional group which can be utilized for binding the compound to a carrier, e.g., unsaturated hydrocarbons, alcohols, amines, thiols, carboxylic acids and derivatives thereof, halides, aldehydes, hydrazids, isocyanates, compounds containing an oxirane ring such as glycidyl ethers, and halogenated silanes. Typical examples of these compounds are, for instance, amines such as n-heptylamine, n-octylamine, decylamine, dodecylamine, hexadecylamine, octadecylamine, 2-aminooctene, naphthylamine, phenyl-n-propylamine and diphenylmethylamine; alcohols such as n-heptyl alcohol, n-octyl alcohol, dodecyl alcohol, hexadecyl alcohol, 1-octene-3-ol, naphthol, diphenylmethanol and 4-phenyl-2-butanol, and glycidyl ethers of these alcohols; carboxylic acids such as n-octanoic acid, nonanoic acid, 2-nonenoic acid, decanoic acid, dodecanoic acid, stearic acid, arachidonic acid, oleic acid, diphenylacetic acid and phenylpropionic acid, and their derivatives such as acid halides, esters and acid amides; halides such as octyl chloride, octyl bromide, decyl chloride and dodecyl chloride; thiols such as octanethiol and dodecanethiol; halogenated silanes such as n-octyltrichlorosilane and octadecyltrichlorosilane; aldehydes such as n-octylaldehyde, n-caprinaldehyde and dodecylaldehyde; and the like.

Besides, there can be used other compounds, e.g., compounds having a log P value of 2.5 or more selected from compounds in which a substituent containing a heteroatom such as halogen, nitrogen, oxygen or sulfur, or other alkyl group, is substituted for hydrogen atom contained in the hydrocarbon moiety of the above-exemplified compounds; and compounds having a log P value of 2.5 or more shown in the above-mentioned review by C. Hansch et al, "PARTITION COEFFICIENTS AND THEIR USES", Chemical Reviews, vol. 71, 525(1971), tables on pages 555 to 613. However, compounds which can be used in the present invention are not limited to these compounds only.

These compounds may be used alone or in an arbitrary combination thereof. Further, these compounds may be used in combination with a compound having a log P value of less than 2.5.

The "water-insoluble carrier" in the adsorbent of the present invention means a carrier which is solid at ordinary temperature under ordinary pressure and is insoluble in water.

The water-insoluble carrier in the present invention may be in the form of, for example, particle, sheet or board, fiber, hollow fiber, and the like, but the form thereof is not limited thereto. The size of the carrier is not also particularly limited.

Typical examples of the water-insoluble carrier used in the present invention are, for instance, inorganic carriers such as glass beads and silica gel; organic carriers each comprising synthetic polymers such as crosslinked polyvinyl alcohol, crosslinked polyacrylate, crosslinked polyacrylamide and crosslinked polystyrene, or polysaccharides such as crystalline celluloses, crosslinked celluloses, crosslinked agarose and crosslinked dextrin; and composite carriers each comprising a combination of the above-mentioned materials such as organic—organic carriers and organic-inorganic carriers.

Among these carriers, hydrophilic carriers are preferable since non-specific adsorption is comparatively a little and the adsorption selectivity for TGF-β is good. The term "hydrophilic carrier" as used herein refers to a carrier composed of a material which has a contact angle with water of 60 degrees or less when the material is shaped into a flat plate. Various methods for measuring the contact angle with water are known, but the most general is a method wherein a water droplet is placed on a plate made of a compound to be measured and the contact angle is measured, as shown in Ikeda, Jikken Kagaku Sensho, Colloid Chemistry, Chapter 4, Thermodynamics of Interface, pages 75–104 (1986) published by Shokabo, Japan. Typical examples of such hydrophilic carriers which are made of a compound having a contact angle with water of at most 60 degrees as measured by this method are, for instance, those comprising cellulose, polyvinyl alcohol, hydrolyzed ethylene-vinyl acetate copolymer, polyacrylamide, polyacrylic acid, polymethacrylic acid, polymethyl methacrylate, polyacrylic acid-grafting polyethylene, polyacrylamide-grafting polyethylene, glass, and the like.

It is more preferable that these water-insoluble carriers have a large number of pores having an adequate size, namely a porous structure. The term "carrier having a porous structure" includes the followings: a carrier comprising globular particles each of which is formed by agglomeration of microglobular particles of a macromolecular material and has spaces (macropores) formed between the agglomerated microglobular particles; a carrier comprising globular particles wherein each microglobular particle contains pores; and a carrier which is made of a homopolymer or copolymer having a three-dimensional network structure (polymer network) and which contains pores (micropores) formed when swollen with an organic solvent having affinity with the homopolymer or copolymer followed by removal of the organic solvent.

Further, from the viewpoint of the adsorption capacity per unit volume of an adsorbent, the water-insoluble carrier having a porous structure is preferred to be porous throughout the entire body rather than only in the surface region. It is also desirable that the pore volume and specific surface area of the carrier are as large as possible so long as the adsorption ability is not impaired.

A typical example of the carrier which satisfies these desirable requirements is a porous cellulose carrier. The porous cellulose carrier has the superior properties that (1) the carrier is hard to be destroyed or to become fine powder by an operation such as agitation because it has a comparatively high mechanical strength and toughness, so when the carrier is packed in a column, compaction and choking of the column do not occur even if a body fluid is flowed at a high flow rate, thus enabling to flow a body fluid at a high rate, and further the porous structure is hard to change by a high pressure steam sterilization or the like, (2) since the carrier is made of a cellulose, it is hydrophilic, and many hydroxyl groups which can be utilized for bonding a ligand are present, and non-specific adsorption hardly occurs, (3) the adsorption capacity which is comparable to a soft carrier can be obtained because the strength is comparatively high even if the pore volume is made large, and (4) the safety is higher than synthetic polymer carriers and the like. Accordingly, a porous cellulose carrier is one of the most suitable carriers, but is not limited thereto. The above-mentioned carriers may be used alone or in combination thereof.

Also, these water-insoluble carriers are desired to have a feature such that a material to be adsorbed can enter pores at some large probability but other proteins enter the pores as little as possible. That is to say, TGF-β which is the subject of adsorption by the adsorbent of the present invention is a protein having a molecular weight of about 25,000, and for efficiently adsorbing this protein, it is preferable that TGF-β can enter the pores at some large probability but other proteins enter the pores as little as possible. Exclusion limit has been generally used as a measure of the molecular weight of a substance which can enter the pores. The term "exclusion limit" means the molecular weight of the smallest molecule of molecules which cannot enter fine pores (namely which are excluded) in a gel permeation chromatography, as described in books (see, for example, Hiroyuki Hatano and Toshihiko Hanai, "Experimental High Performance Liquid Chromatography", Kagaku Dojin). In general, the exclusion limit has been well examined with use of globular protein, dextran, polyethylene glycol or the like. In the case of the water-insoluble porous carrier used in the present invention, it is suitable to use the values obtained by using globular protein.

As a result of study using carriers of various exclusion limits, it has been found that the range of exclusion limit based on globular protein suitable for adsorbing TGF-β is from 5,000 to 600,000. If a carrier having an exclusion limit of less than 5,000 is used, the amount of TGF-β adsorbed is small, so the practicability becomes low. If a carrier having an exclusion limit of more than 600,000 is used, proteins (mainly albumin) other than TGF-β are adsorbed in an increased amount, so the practicability is low from the viewpoint of selectivity. Accordingly, the exclusion limit of the carrier used in the present invention is preferably from 5,000 to 600,000, more preferably from 6,000 to 400,000, the most preferably from 10,000 to 300,000.

Further it is preferable that the carrier has a functional group which can be used in a reaction for immobilizing a ligand to the carrier. Typical examples of the functional group are, for instance, hydroxyl group, amino group, aldehyde group, carboxyl group, thiol group, silanol group, amide group, epoxy group, halogen, succinylimide group, acid anhydride group, and the like. The functional groups are not limited to the exemplified groups.

Any of a hard carrier and a soft carrier can be used as the water-insoluble carrier in the present invention. In the case of use as an adsorbent for an extracorporeal circulation, it is important that the adsorbent does not clog up when it is charged in a column and a fluid is passed through the column. For this purpose, a sufficient mechanical strength is required for the adsorbent. Accordingly it is more preferable that the water-insoluble carrier used in the present invention is a hard carrier. The term "hard carrier" as used herein refers to, for example, in the case of a granular carrier, a carrier which has such a property that a linear relation between pressure drop $\Delta P$ and flow rate is held up to a pressure drop of 0.3 $kg/cm^2$ when the carrier is uniformly charged in a cylindrical column and an aqueous fluid is passed through it, as shown in Reference Example described after.

The adsorbent of the present invention is obtained by immobilizing a compound having a log P value of 2.50 or more on a water-insoluble carrier. Various known methods of immobilization can be used without particular restriction. However, when the adsorbent of the present invention is used for an extracorporeal circulation treatment, it is important from the viewpoint of safety to suppress the elimination or elution of a ligand as much as possible in sterilization or treatment. For this purpose, preferably the immobilization is conducted by a covalent bond method.

Various methods are adoptable for adsorbing and removing TGF-β from a body fluid by using the adsorbent of the present invention. The most simple method is a method wherein a body fluid is taken out and placed in a bag or the like and the adsorbent is mixed therewith to allow to adsorb TGF-β and then the adsorbent is filtered off to obtain the body fluid from which TGF-β has been removed. Another method is a method wherein the adsorbent is packed in a container which has an inlet and an outlet for a body fluid and which is equipped at least at the outlet with a filter which can pass a body fluid but cannot pass the adsorbent, and the body fluid is passed through the container. Both methods can be used, but the latter method is adequate for the adsorbent of the present invention, since the operation is simple and TGF-β can be removed efficiently in on-line system from a body fluid, especially blood, of a patient by incorporating the method into an extracorporeal circulation circuit.

In the extracorporeal circulation circuit as herein referred to, the adsorbent of the present invention can be used not only singly but also in combination with other extracorporeal circulation therapy systems. As an example of the combination use is mentioned an artificial dialysis circuit, and the adsorbent can be used in a combination with dialysis therapy.

An adsorber for TGF-β of the present invention using the TGF-β adsorbent mentioned above will be explained below with reference to FIG. 1 which is a schematic section view showing an example of the adsorber. In FIG. 1, 1 denotes an inlet for a body fluid, 2 denotes an outlet for the body fluid, 3 denotes the TGF-β adsorbent of the present invention, 4 and 5 denote a filter (filter for preventing the adsorbent from flowing out) which can pass a body fluid and components included therein but cannot pass the adsorbent, 6 denotes a column, and 7 denotes an adsorber for TGF-β. The TGF-β adsorber of the present invention is not limited to such an exemplified adsorber, and any devices can be used so long as the devices have a structure that the adsorbent mentioned before is packed in a container having an inlet and an outlet for a body fluid and equipped with a means for preventing the adsorbent from flowing out of the container.

Examples of the means for preventing the adsorbent from flowing out are, for instance, filters such as mesh, nonwoven fabric and cotton stopper. There is no particular limitation in the shape, material and size of the container, but regarding the shape of the container, a cylindrical container is preferred. Preferable materials of the container are those having a sterilization-resistance. Typical examples of such materials are, for instance, glass coated with a silicone, polypropylene, polyvinyl chloride, polycarbonate, polysulfone, polymethylpentene, and the like. It is also preferable that the container has a capacity of about 50 to about 1,500 ml and a diameter of about 2 to about 20 cm, especially a capacity of 100 to 800 ml and a diameter of 3 to 15 cm, more especially a capacity of 150 to 400 ml and a diameter of 4 to 10 cm.

The present invention is more specifically described and explained by means of the following Examples, but it is to be understood that the invention is not limited to only these Examples.

REFERENCE EXAMPLE

Cylindrical glass columns (inner diameter 9 mm, length 150 mm) equipped with filters having a pore size of 15 μm at both ends, were charged uniformly with each of an agarose gel (Biogel A-5m made by Bio-Rad Laboratories, U.S.A., particle size 50 to 100 meshes), a vinyl polymer gel (TOYOPEARL HW-65 made by TOSOH Corporation, Japan, particle size 50 to 100 μm) and a cellulose gel (CELLULOFINE GC-700m made by Chisso Corporation, Japan, particle size 45 to 105 μm). The relationship between flow rate and pressure drop ΔP was determined by passing water through the column with a peristatic pump. The results are shown in FIG. 2.

Figure 2:
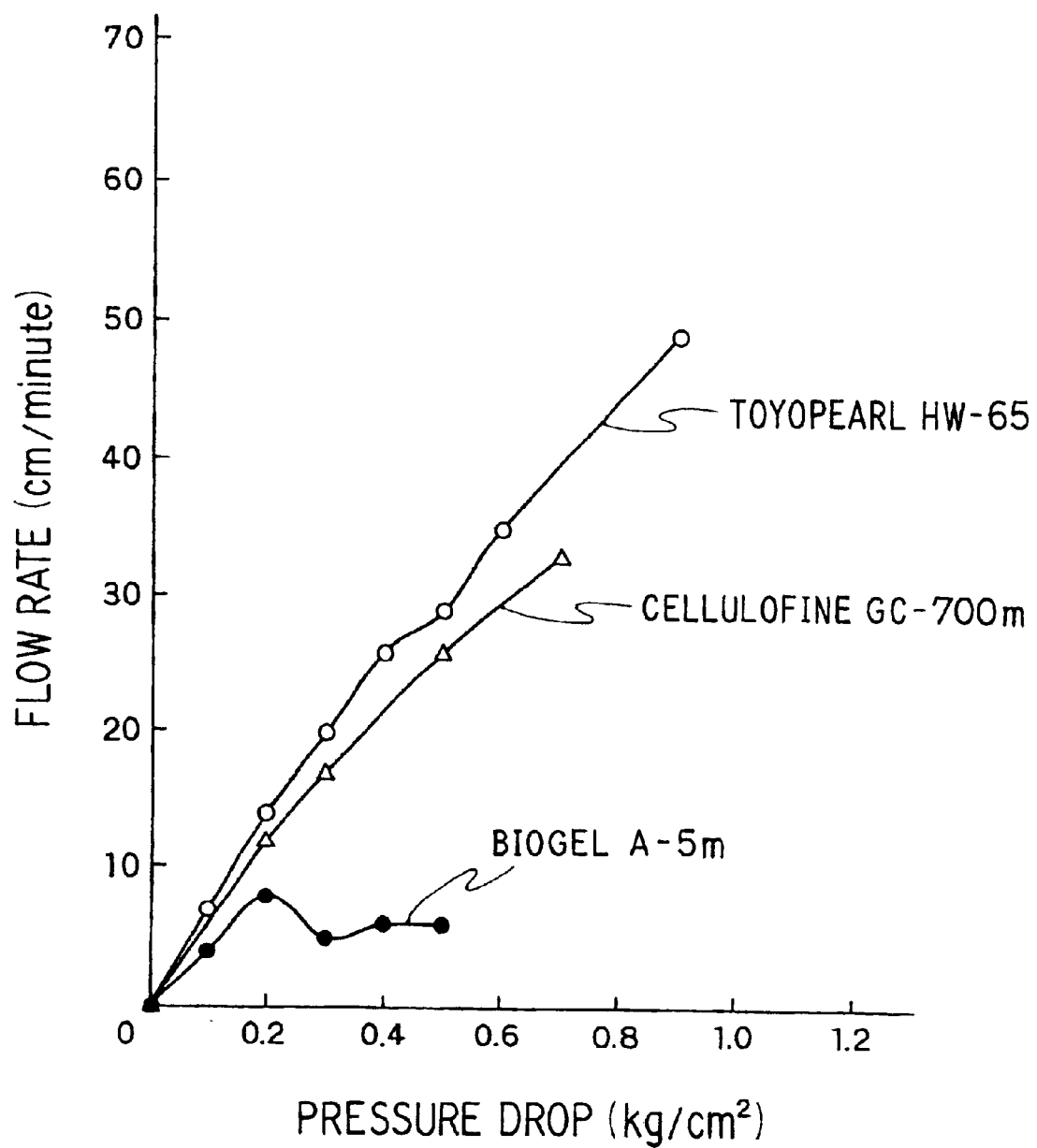
FIG. 2 is a graph showing results of examining a relationship between the flow rate and the pressure drop by using three kinds of water-insoluble carriers.

In FIG. 2, it is found that TOYOPEARL HW-65 and CELLULOFINE GC-700 m show that the flow rate increases almost in proportion to an increase in pressure, whereas Biogel A-5m causes a compaction and the flow rate does not increase even if the pressure is increased. In the present invention, a gel showing that the relationship between the pressure drop ΔP and the flow rate is linear up to a pressure drop of 0.3 kg/cm$^2$, like the former, is referred to as a hard gel.

Example 1

Water was added to 170 ml of a porous cellulose gel (CELLULOFINE GC-200 m made by Chisso Corporation, Japan, exclusion limit for a globular protein 140,000) up to the total amount of 340 ml. Thereto was added 90 ml of a 2M aqueous solution of sodium hydroxide, and the mixture was kept at 40° C. To the mixture was then added 31 ml of epichlorohydrin, and the reaction was carried out with stirring at 40° C. for 2 hours. After the completion of the reaction, the gel was thoroughly washed with water to give an epoxidized cellulose gel (epoxidized CELLULOFINE GC-200m).

To 10 ml of the epoxidized cellulose gel was added 200 mg of n-hexadecylamine (Σf=7.22), and the mixture was allowed to stand for reaction in ethanol at 45° C. for 6 days to immobilize the amine onto the cellulose gel as a carrier. After the completion of the reaction, the gel was thoroughly washed with ethanol and water in that order to give an n-hexadecylamine-immobilized cellulose gel.

To 0.5 ml of the thus obtained immobilized gel (adsorbent) was added 3 ml of a normal human serum (made by Dainippon Pharmaceutical Co., Ltd.) containing 500 pg/ml of a human TGF-β1 (derived from human platelet, product of Pharma Biotechnologies Hannover GmbH). The resulting mixture was shaken at 37° C. for 2 hours. The concentration of TGF-β1 in the supernatant was measured by using an ELISA kit (made by Biosource International INC).

The result is shown in Table 1.

Example 2

An epoxidized cellulose gel (epoxidized CELLULOFINE GC-200m) was prepared in the same manner as in Example 1.

To 10 ml of the epoxidized cellulose gel was added 200 mg of n-octylamine (log P=2.90), and the mixture was allowed to stand in a 50 v/v % aqueous solution of ethanol at 45° C. for 6 days for reaction. After the completion of the reaction, the gel was thoroughly washed with a 50 v/v % aqueous ethanol solution, ethanol, a 50 v/v % aqueous ethanol solution and water in that order to give an n-octylamine-immobilized cellulose gel.

Adsorption test was made in the same manner as in Example 1 by using the thus obtained adsorbent, and the concentration of TGF-β1 in the supernatant was measured.

The result is shown in Table 1.

Comparative Example 1

An n-hexylamine-immobilized cellulose gel was prepared in the same manner as in Example 2 except that n-hexylamine (log P=2.06) was used instead of n-octylamine (log P=2.90). Adsorption test was made in the same manner as in Example 1 by using this adsorbent.

The result of the measurement of the concentration of TGF-β1 in the supernatant is shown in Table 1.

Comparative Example 2

An n-butylamine-immobilized cellulose gel was prepared in the same manner as in Example 2 except that n-butylamine (log P=0.97) was used instead of n-octylamine (log P=2.90). Adsorption test was made in the same manner as in Example 1 by using this adsorbent.

The result of the measurement of the concentration of TGF-β1 in the supernatant is shown in Table 1.

Comparative Example 3

Adsorption test was made in the same manner as in Example 1 except that a porous cellulose gel (CELLULOFINE GC-200m) was used instead of the immobilized cellulose gel (immobilized CELLULOFINE GC-200m).

The result of the measurement of the concentration of TGF-β1 in the supernatant is shown in Table 1.

TABLE 1

|  | Concentration of TGF-β1 in the supernatant |
|---|---|
| Example 1 | 53 pg/ml |
| Example 2 | 191 pg/ml |
| Comparative Example 1 | 456 pg/ml |
| Comparative Example 2 | 473 pg/ml |
| Comparative Example 3 | 482 pg/ml |

Example 3

An n-hexadecylamine-immobilized cellulose gel (n-hexadecylamine-immobilized CELLULOFINE GC-200m) was prepared in the same manner as in Example 1.

To 0.5 ml of the thus obtained immobilized gel (adsorbent) was added 3 ml of a normal human serum (made by Dainippon Pharmaceutical Co., Ltd.) containing 500 pg/ml of a human TGF-β3 (recombinant, product of R & D Systems Corporation). The resulting mixture was shaken at 37° C. for 2 hours. The concentration of TGF-β3 in the supernatant was measured by an ELISA method.

The ELISA method was conducted as follows: Onto an ELISA plate were distributed 0.1 ml portions of a solution of an anti-human TGF-β antibody (product of R & D Systems Corporation). After allowing to stand overnight at room temperature, the plate was washed, and 0.3 ml portions of a solution of bovine serum albumin were distributed onto the plate. After allowing to stand at room temperature for 1 hour, the plate was washed, and 0.1 ml of the specimen (supernatant) was added to the plate. The plate was allowed to stand at room temperature for 2 hours and washed, and 0.1 ml portions of a solution of a biotin-labeled anti-human TGF-β3 antibody (product of R & D Systems Corporation) were distributed onto the plate. After allowing to stand at room temperature for 2 hours, the plate was washed. Thereto was then added a streptavidin HRP solution, and the plate was allowed to stand at room temperature for 20 minutes. After washing the plate, 0.1 ml portions of a substrate solutions were distributed to the plate. After allowing to stand at room temperature for 20 minutes, 0.1 ml portions of 0.5N sulfuric acid were distributed to the plate and the absorbance was measured at 450 nm. The concentration of TGF-β in the specimen (supernatant) was obtained by comparison with the absorbance of the standard liquids with known concentrations.

The result is shown in Table 2.

Example 4

The treatment of a normal human serum containing a human TGF-β3 and the measurement of TGF-β3 concentration in the supernatant were conducted in the same manner as in Example 3 except that the n-octylamine-immobilized cellulose gel (n-octylamine-immobilized CELLULOFINE GC-200m) obtained in Example 2 was used as an adsorbent.

The result is shown in Table 2.

Comparative Example 4

The treatment of a normal human serum containing a human TGF-β3 and the measurement of TGF-β3 concentration in the supernatant were conducted in the same manner as in Example 3 except that the n-hexylamine-immobilized cellulose gel (n-hexylamine-immobilized CELLULOFINE GC-200m) obtained in Comparative Example 1 was used as an adsorbent.

The result is shown in Table 2.

Comparative Example 5

The treatment of a normal human serum containing a human TGF-β3 and the measurement of TGF-β3 concentration in the supernatant were conducted in the same manner as in Example 3 except that the n-butylamine-immobilized cellulose gel (n-butylamine-immobilized CELLULOFINE GC-200m) obtained in Comparative Example 2 was used as an adsorbent.

The result is shown in Table 2.

Comparative Example 6

The treatment of a normal human serum containing a human TGF-β3 and the measurement of TGF-β3 concentration in the supernatant were conducted in the same manner as in Example 3 except that a non-immobilized cellulose gel (CELLULOFINE GC-200m) was used instead of the immobilized cellulose gel.

The result is shown in Table 2.

TABLE 2

|  | Concentration of TGF-β3 in the supernatant |
|---|---|
| Example 3 | 48 pg/ml |
| Example 4 | 182 pg/ml |
| Comparative Example 4 | 450 pg/ml |
| Comparative Example 5 | 474 pg/ml |
| Comparative Example 6 | 479 pg/ml |

As apparent from the results shown in Tables 1 and 2, TGF-β can be efficiently adsorbed and removed from a body fluid by the adsorbent of the present invention comprising a water-insoluble carrier and a compound having a log P value of 2.50 or more immobilized on the carrier.

What we claim is:

1. A method for removing a transforming growth factor-β from a body fluid, which comprises:
   removing body fluid from a living body, wherein the body fluid is selected from the group consisting of plasma, serum, ascites, lymph and synovia,
   bringing the body fluid into contact with an adsorbent comprising (i) a porous cellulose carrier, and (ii) a compound immobilized on said carrier and having a log P value of at least 2.50 wherein P is a partition coefficient in an octanol-water system, and
   returning the body fluid to the living body.

2. The method of claim 1, which incorporates an extracorporeal circulation circuit used in combination with another extracorporeal circulation therapy.

* * * * *